United States Patent [19]

Nofre et al.

[11] Patent Number: 5,480,668
[45] Date of Patent: Jan. 2, 1996

[54] N-SUBSTITUTED DERIVATIVES OF ASPARTAME USEFUL AS SWEETENING AGENTS

[76] Inventors: Claude Nofre, 119 Cours Albert Thomas, 69003 Lyon; Jean-Marie Tinti, 5 Impasse de la Drelatière, 69680 Chassieu, both of France

[21] Appl. No.: 149,365

[22] Filed: Nov. 9, 1993

[30] Foreign Application Priority Data

Nov. 12, 1992 [FR] France ................................. 92 13615

[51] Int. Cl.$^6$ ................................. A23L 1/236
[52] U.S. Cl. ..................... 426/548; 544/322; 558/412; 558/413; 558/414; 558/418
[58] Field of Search ............ 426/548; 544/322; 558/412, 413, 414, 418

[56] References Cited

U.S. PATENT DOCUMENTS

| | | | |
|---|---|---|---|
| 3,475,403 | 10/1969 | Mazur et al. | 426/548 |
| 3,492,131 | 1/1970 | Schlatter | 426/548 |
| 4,645,678 | 2/1987 | Nofre et al. | |
| 4,673,582 | 6/1987 | Nofre et al. | 426/548 |
| 4,877,895 | 10/1989 | Nofre et al. | 558/413 |
| 4,921,939 | 5/1990 | Nofre et al. | 558/414 |
| 4,935,517 | 6/1990 | Nofre et al. | |
| 4,997,667 | 3/1991 | Nofre et al. | 426/548 |
| 5,196,540 | 3/1993 | Nofre et al. | 546/309 |
| 5,272,272 | 12/1993 | Nofre et al. | 546/289 |
| 5,310,908 | 5/1994 | Nofre et al. | 544/335 |
| 5,374,733 | 12/1994 | Nofre et al. | 546/294 |

FOREIGN PATENT DOCUMENTS

334236A2  9/1989  European Pat. Off. .

OTHER PUBLICATIONS

Janusz, J. M. 1989 "Peptide Sweeteners Beyond Aspartame" in *Progress in Sweeteners* Ed. T. H. Grenby, Elsevier, London, pp. 1–46.

Mazur et al., 1969. "Structure–Taste Reletionships of Some Dipeptides". J. of the American Chemical Society, 91:10, pp. 2684–2691.

Novel Inhibitors of Enkephalin–Degrading Enzumes III: 4–Carboxymethylamino–4–oxo–3 (Phenylamino) Butanoic Acids as Enkephalinase Inhibitors, vol. 5, pp. 133–149, 1991 (A. Patel, H. J. Smith and R. D. E. Sewell).

*Primary Examiner*—Helen Pratt
*Attorney, Agent, or Firm*—Armstrong, Westerman, Hattori, McLeland & Naughton

[57] ABSTRACT

Lower alkyl esters of compounds of the formula

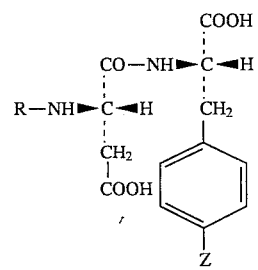

wherein Z is hydrogen or hydroxyl and R is a hydrocarbyl group optionally substituted by hydroxy and/or alkoxy group, are useful as sweetening agents.

7 Claims, 2 Drawing Sheets

COMPARATIVE STABILITY (pH 3, 70 °C)

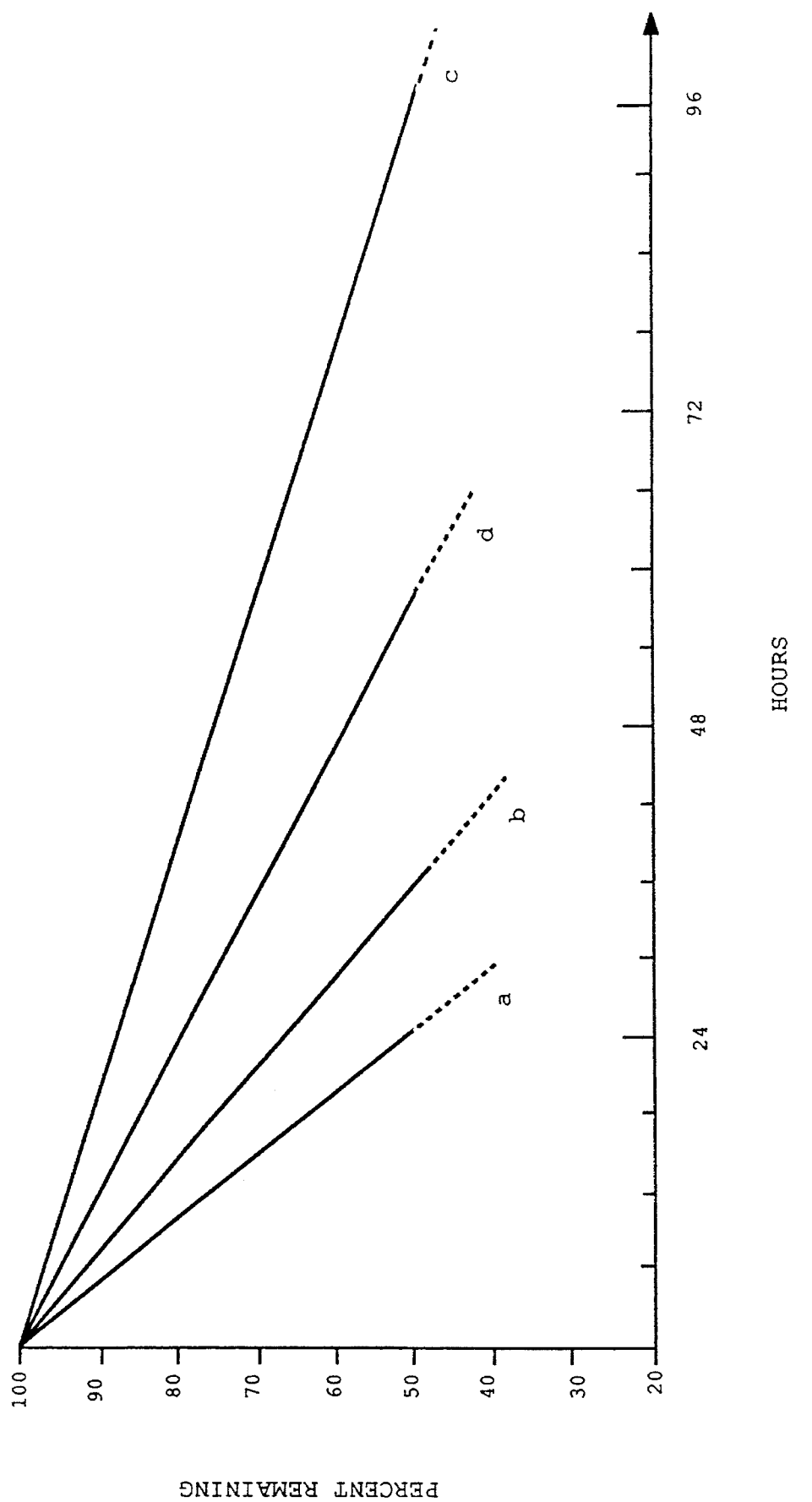

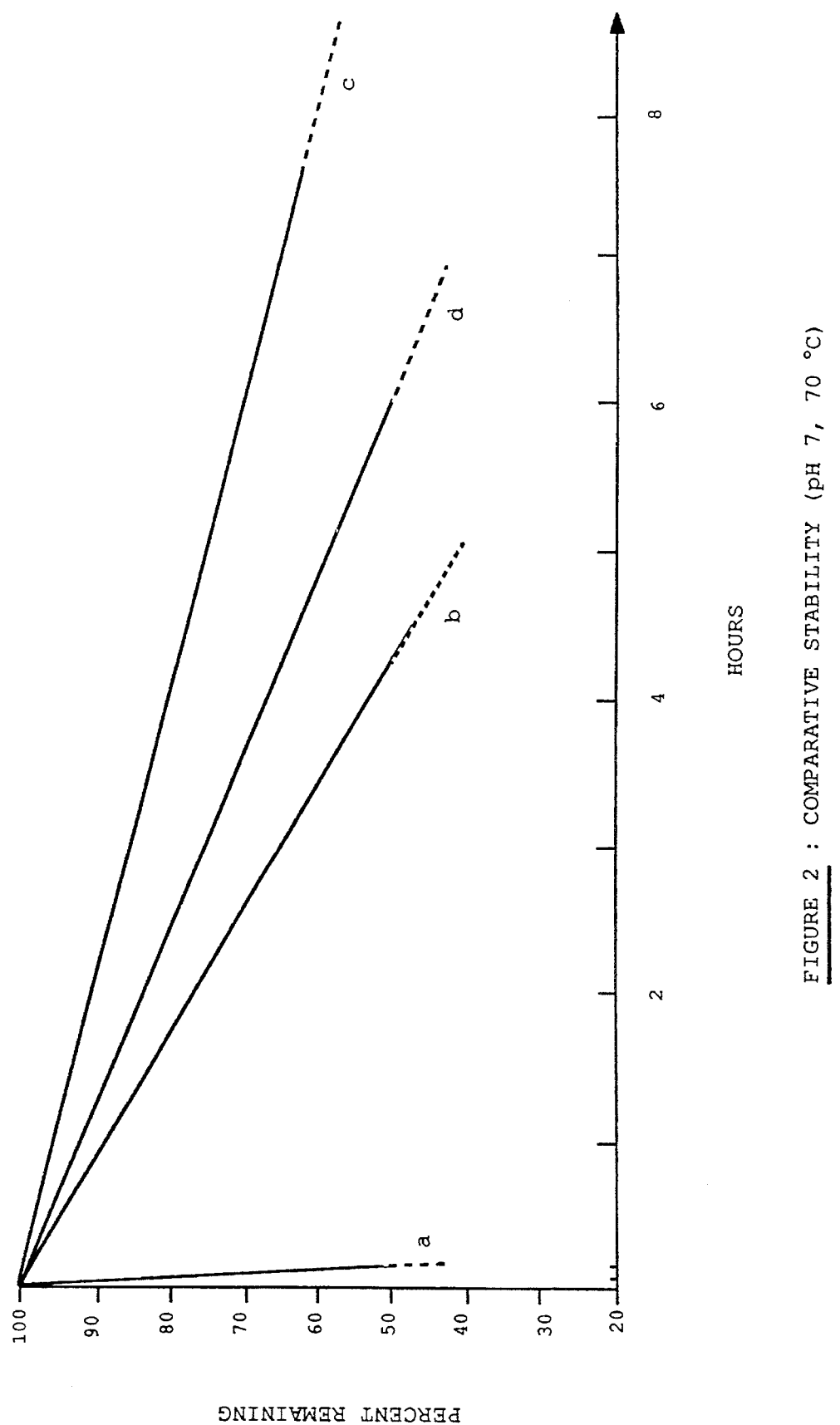
FIGURE 2 : COMPARATIVE STABILITY (pH 7, 70 °C)

N-SUBSTITUTED DERIVATIVES OF ASPARTAME USEFUL AS SWEETENING AGENTS

BACKGROUND OF THE INVENTION

1. Field of the Invention

The present invention relates to novel compounds derived from aspartame which are useful as sweetening agents and to their method of preparation.

These novel compounds are particularly useful for sweetening a variety of products, especially drinks, foods, confectionery, pastries, chewing gums, hygiene products and toiletries, as well as cosmetic, pharmaceutical and veterinary products.

It is known that, to be usable on the industrial scale, a sweetening agent must possess firstly an intense sweetening potency, making it possible to limit the cost of use, and secondly a satisfactory stability, i.e. a stability compatible with the conditions of use.

2. Discussion of the Prior Art

The dipeptide derivative N-L-α-aspartyl-phenylalanine 1-methyl ester, known by the name aspartame and having the following formula:

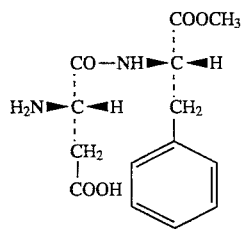

is the most widely used at the present time among the sweetening agents currently on the market (U.S. Pat. No. 3,492,131). One of the great assets of this compound is its chemical constitution based on two natural amino acids, namely L-aspartic acid and L-phenylalanine. The relatively weak sweetening potency of this compound is about 120 to 180 times that of sucrose on a weight basis. Despite excellent organoleptic properties, the main disadvantages of this compound are that it is an expensive product on account of its relatively low sweetening intensity, and that it has a rather low stability under certain conditions of use of sweetening agents, especially in neutral media, limiting its areas of industrial application.

Consequently the food industry has an apparent need for a new sweetening agent which has a high sweetening activity, so as to reduce its cost price, and which is at least as stable as aspartame, if not more stable, especially in neutral media. Thus numerous sweet dipeptides or dipeptide analogs have since been synthesized (see, for example, J. M. Janusz in Progress in Sweeteners, Ed. T. H. Grenby, Elsevier, London, 1989, pp. 1–46), but hitherto, with the exception of aspartame, none of them has seemed to satisfy the main requirements of a sweetening agent, namely excellent organoleptic properties, a sufficiently high sweetening intensity to reduce the cost of use, and a sufficient stability.

SUMMARY OF THE INVENTION

It has been discovered, quite unexpectedly, that the sweetening potency of aspartame can be very greatly enhanced by attaching certain radicals, especially appropriately selected hydrocarbon radicals, to the free amine of aspartame; in this way the sweetening potency of aspartame can be increased by a factor of up to 80, the sweetening intensity varying according to the specific nature of the radical R. It is this discovery which forms the basis of the present invention.

Results of the same nature have been observed with the ethyl, isopropyl, propyl and tert-butyl esters of N-L-α-aspartyl-L-phenylalanine (U.S. Pat. No. 3,492,131) and with N-L-α-aspartyl-L-tyrosine 1-methyl ester (U.S. Pat. No. 3,475,403).

According to a first feature, the aim of the present patent application is therefore to cover the compounds of the formula

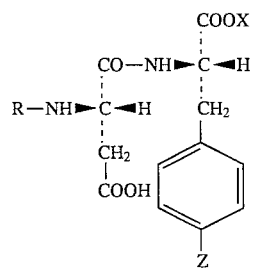

in which R is selected from $CH_3(CH_2)_2CH_2$, $(CH_3)_2CHCH_2$, $(CH_3)_2CHCH_2CH_2$, $CH_3CH_2CH(CH_3)CH_2$, $(CH_3CH_2)_2CHCH_2$, $(CH_3)_3CCH_2CH_2$, cyclohexyl, cycloheptyl, cyclooctyl, cyclopentylmethyl, cyclohexylmethyl, 3-phenylpropyl, 3-methyl-3-phenylpropyl, 3,3-dimethylcyclopentyl, 3-methylcyclohexyl, 3,3,5,5-tetramethylcyclohexyl, 2-hydroxycyclohexyl, 3-(4-hydroxy-3-methoxyphenyl)propyl, 3-(4-hydroxy-3-methoxyphenyl)-2-propenyl, 3-(4-hydroxy-3-methoxyphenyl)-1-methylpropyl and 3-(4-hydroxy-3-methoxyphenyl)-1-methyl-2-propenyl groups, X is selected from $CH_3$, $CH_2CH_3$, $CH(CH_3)_2$, $CH_2CH_2CH_3$ and $C(CH_3)_3$ groups and Z is a hydrogen atom or an OH group, and the physiologically acceptable salts of these compounds.

N-Substituted aspartame derivatives with a high sweetening potency have already been described in the prior art. Thus the document EP-0 107 597 (U.S. Pat. No. 4,645,678) describes N-phenylcarbamoyl or N-phenylthiocarbamoyl compounds of aspartame whose sweetening potency can be as much as 55,000 times that of sucrose. However, there is no structural similarity between these N-phenylcarbamoyl or N-phenylthiocarbamoyl groups and the N-hydrocarbon groups of the compounds of the invention.

Other N-substituted aspartame derivatives have also been described (see, for example, J. M. Janusz, op. cit.), but these compounds again have no structural relationship with the N-hydrocarbon derivatives of the invention.

In actual fact, there was a prejudice in the state of the art which has hitherto dissuaded those skilled in the art from directing their attention towards the search for N-hydrocarbon derivatives of aspartame with a high sweetening potency. Thus the only N-hydrocarbon derivative of aspartame described in the literature, namely N-[N,N-dimethyl-L-α-aspartyl]-L-phenylalanine 1-methyl ester of the following formula:

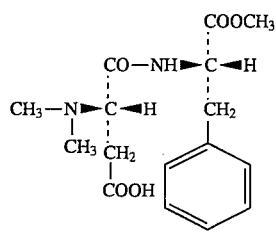

is described as having a bitter taste (R. H. Mazur et al., J. Amer. Chem. Soc., 1969, 91, 2684–2691).

Moreover, the researches conducted by the present inventors have led to the observation that the organoleptic properties of N-hydrocarbon derivatives of aspartame are totally unpredictable and that hydrocarbon groups which are structurally very similar give rise to aspartame derivatives which can be sweet, bittersweet, bitter or tasteless, as the case may be. Furthermore, in the document EP-0 338 946 (U.S. Pat. No. 4,935,517), the Applicants described N-hydrocarbon derivatives of L-aspartic acid (n=1) or L-glutamic acid (n=2) having the following general formula:

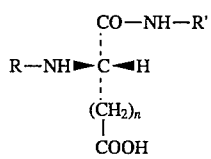

in which the radical R is a saturated or unsaturated acyclic, cyclic or mixed hydrocarbon group having five to thirteen carbon atoms, the radical R' is a 4-cyanophenyl, 2-cyanopyrid-5-yl or 2-cyanopyrimidin-5-yl group and n is equal to 1 or 2.

The compounds of the invention differ from these compounds of the prior art in that they are specifically L-aspartic acid compounds, they contain a group R' which has no structural analogy with those defined in the document EP-0 338 946, and their activity depends on the selection of very specific N-hydrocarbon groups.

The studies of structure/activity relationships carried out by the present inventors have in fact led to the observation that the most effective N-hydrocarbon groups in the prior art document EP-0 338 946 give rise to bitter or bittersweet compounds when combined with aspartame. This is especially true of the n-heptyl group, which gives rise to one of the sweetest compounds in the prior art document, but which gives a compound with a very strong bitter aftertaste when combined with aspartame.

It has also been demonstrated that the stability of the compounds characteristic of the invention is higher than that of aspartame under the common conditions of use for food preparations. This advantage is all the more important because one of the factors limiting the use of aspartame in certain food preparations originates from its very low stability in media close to neutrality, i.e. for pH values of around 7, which are frequently encountered in products such as dairy products, pastries or other preparations which require high-temperature cooking, chewing gums and toothpastes.

An accelerated aging study by the prolonged heating at 70° C. of an aqueous solution at pH 7 of a compound characteristic of the invention, namely N-[N-(3,3-dimethylbutyl)-L-α-aspartyl]-L-phenylalanine 1-methyl ester, whose sweetening potency is 10,000 times higher than that of sucrose, shows a half-life of about 6 hours, whereas the half-life of aspartame under the same conditions is only 10 minutes; the stability of the compound according to the invention is thus 36 times higher than that of aspartame. Comparable results have been obtained for the other compounds characteristic of the invention.

It has also been demonstrated that the stability of the compounds of the invention is at least as high, if not higher, in acid media at a pH of around 3, corresponding to the pH of the soft drinks which represent one of the major applications of sweetening agents.

By virtue of their high sweetening potency, another advantage of the compounds of the invention compared with aspartame is that, in their application to food products, they make it possible to use very small amounts of active agent. Consequently the often debated presence of certain constituents of aspartame, namely L-phenylalanine and methanol, in food products will be very greatly reduced by using a sweetening agent of the present invention. Thus, for example, it will be possible to replace 550 mg of aspartame, in one liter of soft drink, with about 7 mg of the N-[N-(3,3-dimethylbutyl)-L-α-aspartyl]-L-phenylalanine 1-methyl ester described in the present invention, and thereby to reduce, by a factor of up to about 80, the amounts of L-phenylalanine and methanol which are liable to be consumed, while at the same time maintaining identical organoleptic properties.

The present invention therefore makes it possible for the first time to provide novel N-hydrocarbon derivatives of aspartame or its analogs which have excellent organoleptic properties associated with a very high sweetening potency of up to 10,000 times the sweetening potency of sucrose on a weight basis, and a stability which is at least similar or greater, the effect of which is to increase the number of possible uses in food preparations, compared with aspartame.

BRIEF DESCRIPTION OF THE DRAWINGS

FIGS. 1 and 2 of the drawings are graphs comparing the stability of characteristic compounds of the invention with that of aspartame.

DESCRIPTION OF PREFERRED EMBODIMENTS

One particularly advantageous embodiment of the invention has the following general formula:

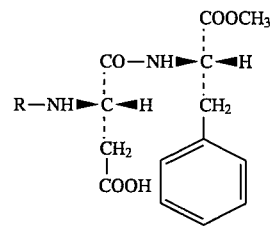

in which R is as defined above.

A compound representing a particularly advantageous embodiment of the invention is N-[N-(3,3-dimethylbutyl)-L-α-aspartyl]-L-phenylalanine 1-methyl ester (compound 6 of Table 1) of the formula

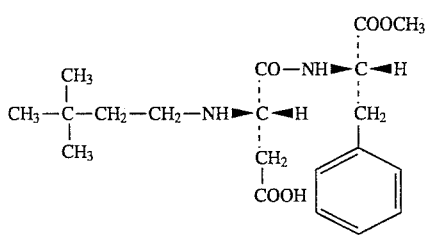

or N-[N-[3-(4-hydroxy-3-methoxyphenyl)propyl]-L-α-aspartyl]-L-phenylalanine 1-methyl ester (compound 18 of Table 1) of the formula

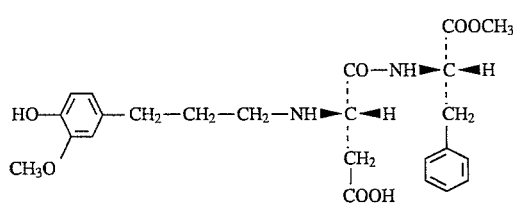

or else N-[N-(3-phenylpropyl)-L-α-aspartyl]-L-phenylalanine 1-methyl ester (compound 12 of Table 1) of the formula

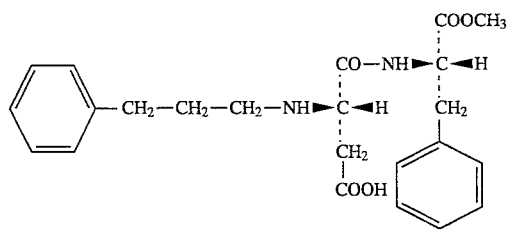

The compounds of the invention car also be salified with physiologically acceptable inorganic or organic acids or bases, the effect of which is to increase their solubility. Advantageously, these compounds are salified in the form of the hydrochloride or the sodium, potassium, ammonium, calcium or magnesium salts.

According to a second feature, the aim of the present patent application is to cover the compounds of the invention as sweetening agents, the sweetening compositions in which at least one compound as defined above is incorporated as the sweetening agent, and the use of the compounds of the invention for sweetening the various products referred to in the introduction.

The sweetening agents of the present invention can be added to any edible product to which it is desired to give a sweet taste, provided they are added in sufficient proportions to achieve the desired level of sweetness. The optimal use concentration of the sweetening agent will depend on a variety of factors such as, for example, the sweetening potency of the sweetening agent, the conditions of storage and use of the products, the particular constituents of the products and the desired level of sweetness. Any qualified person can easily determine the optimal proportion of sweetening agent which must be employed to obtain an edible product, by performing routine sensory analyses. The sweetening agents of the present invention will generally be added to the edible products in proportions ranging from 0.5 mg to 50 mg of sweetening agent per kilogram or per liter of edible product, depending on the sweetening potency of the compound. The concentrated products will obviously contain larger amounts of sweetening agent and will then be diluted in accordance with the intended final uses.

The sweetening agents of the present invention can be added in the pure form to the products to be sweetened, but because of their high sweetening potency, they are generally mixed with an appropriate carrier or bulking agent.

Advantageously, the appropriate carriers or bulking agents are selected from the group consisting of polydextrose, starch, maltodextrins, cellulose, methylcellulose, carboxymethylcellulose and other cellulose derivatives, sodium alginate, pectins, gums, lactose, maltose, glucose, leucine, glycerol, mannitol, sorbitol, sodium bicarbonate, phosphoric, citric, tartaric, fumaric, benzoic, sorbic and propionic acids and their sodium, potassium and calcium salts, and equivalents thereof.

The sweetening agents according to the invention can be employed in an edible product by themselves, as the only sweetening agent, or in combination with other sweetening agents such as sucrose, corn syrup, fructose, sweet dipeptide derivatives or analogs (aspartame, alitame), neohesperidin dihydrochalcone, hydrogenated isomaltulose, stevioside, the L sugars, glycyrrhizin, xylitol, sorbitol, mannitol, acesulfame, saccharin and its sodium, potassium, ammonium and calcium salts, cyclamic acid and its sodium, potassium and calcium salts, sucralose, monellin, thaumatin and equivalents thereof.

The compounds of the present invention can be prepared by various methods already described in the literature. Thus, according to a third feature, the aim of the present patent application is to cover one of the preferred methods, which consists in condensing a compound of the formula

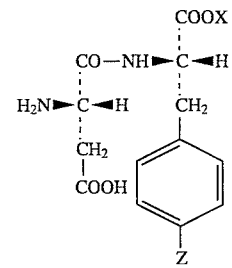

with an aldehyde or ketone compound which is a precursor of the group R. The intermediate imine formed by condensation is then reduced in situ with a selective reducing agent, for example sodium cyanoborohydride, to give the compounds of the invention directly (reductive N-monoalkylation method described by Ohfune et al., Chemistry Letters, 1984, 441–444).

A compound of the invention in which R is the radical $(CH_3)_3CCH_2CH_2$, for example, is obtained from the commercial aldehyde precursor 3,3-dimethylbutyraldehyde of the formula $(CH_3)_3CCH_2CHO$.

It should be noted that the compounds of the invention are prepared directly from aspartame or its analogs. As far as aspartame derivatives are concerned, this is a particularly valuable advantage for the reason that aspartame is a commercial product whose synthesis has now been mastered to perfection.

The purification of the compounds of the invention, in their acid or salt form, is carried out by the standard techniques such as recrystallization or chromatography. Their structure and their purity were checked by the conventional techniques (thin layer chromatography, high performance liquid chromatography, infrared spectrometry, nuclear magnetic resonance, elemental analysis).

The way in which the invention can be carried out and the advantages which result therefrom will become more clearly apparent from the practical Examples which follow.

In these Examples, the sweetening potency of the compounds described was evaluated by a team of eight experienced people. This was done by comparing the taste of the compounds, in aqueous solution at variable concentrations, with a 2%, 5% or 10% reference solution of sucrose. The sweetening potency of the test compound compared with sucrose then corresponds to the weight ratio between the compound and sucrose for equal sweetening intensity, i.e. when the sweet tastes of the solution of the test compound and the reference solution of sucrose are considered by a majority of people to have the same sweetening intensity.

The stability of the compounds of the invention and aspartame was measured using high performance liquid chromatography (HPLC) to determine the amount of product remaining after accelerated aging in an acid medium (phosphate buffer at pH 3) or in a neutral medium (phosphate buffer at pH 7) at a temperature of 70° C. The stability of the compound tested in this way is evaluated by its half-life (time corresponding to 50% degradation).

As a Preparatory Example, N-[N-(3,3-dimethylbutyl)-L-α-aspartyl]-L-phenylalanine 1-methyl ester (Example no. 6 of Table 1) of the formula

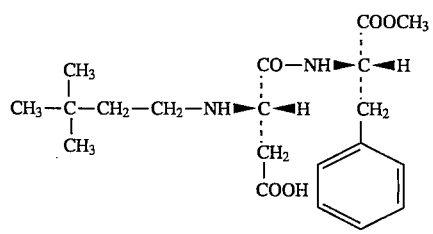

is synthesized as follows:

Four grams (39.8 mmol) of 3,3-dimethylbutyraldehyde of commercial origin are added to a mixture of 10.6 g (36.2 mmol) of aspartame and 1.6 g (25.3 mmol) of sodium cyanoborohydride in 50 cm³ of methanol. The solution is stirred for 24 hours at room temperature and then concentrated to dryness under vacuum. The residue is then taken up in a 1N aqueous solution of hydrochloric acid until the pH is approximately neutral. The gummy precipitate formed is filtered off, dried under vacuum and recrystallized from an ethanol/water mixture (1/1) or from acetonitrile to give 9 g (yield 62%) of N-[N-(3,3-dimethylbutyl)-L-α-aspartyl]-L-phenylalanine 1-methyl ester.

On a weight basis, the sweetening potency of this compound corresponds approximately to 10,000 times that of sucrose by comparison with 2%, 5% and 10% solutions of sucrose.

By comparison with aspartame, an aqueous solution of 7 mg/l of the present compound is equivalent in terms of sweetening intensity to a solution of 550 mg/l of aspartame, which corresponds to a sweetening potency about 80 times higher than that of aspartame.

Table 1 gives, by way of example, the sweetening potency of other compounds according to the invention obtained from aspartame by an experimental protocol similar to that described above, which will be readily accessible to those skilled in the art. The sweetening potency was evaluated relative to a 2% solution of sucrose.

TABLE 1

R—NH—CH(CH₂COOH)—CO—NH—CH(COOCH₃)—CH₂—C₆H₅

| No. | R | Sweetening Potency |
|---|---|---|
| 1 | CH₃CH₂CH₂CH₂ | 400 |
| 2 | (CH₃)₂CHCH₂ | 500 |
| 3 | (CH₃)₂CHCH₂CH₂ | 1 300 |
| 4 | (R,S)-CH₃CH₂CH(CH₃)CH₂ | 900 |
| 5 | (CH₃CH₂)₂CHCH₂ | 2 000 |
| 6 | (CH₃)₃CCH₂CH₂ | 10 000 |
| 7 | cyclohexyl | 800 |
| 8 | cycloheptyl | 900 |
| 9 | cyclooctyl | 1 000 |
| 10 | cyclopentylmethyl | 1 500 |
| 11 | cyclohexylmethyl | 800 |
| 12 | C₆H₅CH₂CH₂CH₂ | 1 500 |
| 13 | (R,S)-C₆H₅CH(CH₃)CH₂CH₂ | 1 200 |
| 14 | 3,3-dimethylcyclopentyl | 150 |
| 15 | (R,S)-3-methylcyclohexyl | 1 000 |
| 16 | 3,3,5,5-tetramethylcyclohexyl | 1 000 |
| 17 | (R,S)-2-hydroxycyclohexyl | 800 |
| 18 | (3-OCH₃,4-OH)C₆H₃CH₂CH₂CH₂ | 2 500 |
| 19 | (3-OCH₃,4-OH)C₆H₃CH=CHCH₂ | 2 000 |
| 20 | (R,S)-(3-OCH₃,4-OH)C₆H₃CH₂CH₂CH(CH₃) | 500 |
| 21 | (R,S)-(3-OCH₃,4-OH)C₆H₃CH=CHCH(CH₃) | 500 |

By way of additional examples of the general formula, the sweetening potency of N-[N-(3,3-dimethylbutyl)-L-α-aspartyl]-L-phenylalanine 1-ethyl ester is 2000 times that of sucrose and the sweetening potency of N-[N-(3,3-dimethylbutyl)-L-α-aspartyl]-L-tyrosine 1-methyl ester is 4000 times that of sucrose (by comparison with a 2% solution of sucrose).

FIG. 1 attached shows a comparative diagram of the stability curves of a few compounds characteristic of the invention compared with aspartame (curve a), the examples taken being compounds 2, 5 and 6 of Table 1 (curves b, c and d respectively), these curves having been obtained during accelerated aging by heating of their solutions at a concentration of 1 g/l, in an acid medium of pH 3, at 70° C. Under these experimental conditions, the half-life of aspartame is about 24 hours, whereas the half-lives of the compounds of the invention are about 35 hours for compound 2, 96 hours for compound 5 and 55 hours for compound 6, corresponding to stabilities which are up to 4 times higher than that of aspartame.

FIG. 2 attached gives a comparative diagram of the stability curves of compounds 2, 5 and 6 of Table 1 (curves b, c and d respectively) compared with aspartame (curve a), these curves having been obtained during accelerated aging by heating of their solutions at a concentration of 1 g/l, in a neutral medium of pH 7, at 70° C. Under these experimental conditions, aspartame has a very low stability (half-life of 10 minutes), whereas the compounds of the invention have half-lives of 4 h 15 min for compound 2, 10 hours for compound 5 and 6 hours for compound 6, corresponding to stabilities which are up to 60 times higher than that of aspartame.

What is claimed is:

1. A compound of the general formula

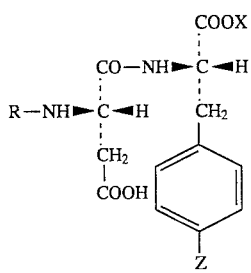

in which R is selected from CH₃(CH₂)₂CH₂, (CH₃)₂CHCH₂, (CH₃)₂CHCH₂CH₂, CH₃CH₂CH(CH₃)CH₂, (CH₃CH₂)₂CHCH₂, (CH₃)₃CCH₂CH₂, cyclohexyl, cycloheptyl, cyclooctyl, cyclopentylmethyl, cyclohexylmethyl, 3-phenylpropyl, 3-methyl-3-phenylpropyl, 3,3-dimethylcyclopentyl, 3-methylcyclohexyl, 3,3,5,5-tetramethylcyclohexyl, 2-hydroxycyclohexyl, 3-(4-hydroxy-3-methoxyphenyl)propyl, 3-(4-hydroxy-3-methoxyphenyl)-2-propenyl, 3-(4-hydroxy-3-methoxyphenyl)-1-methylpropyl and 3-(4-hydroxy-3-methoxyphenyl)-1-methyl-2-propenyl groups, X is selected from CH₃, CH₂CH₃, CH(CH₃)₂, CH₂CH₂CH₃ and C(CH₃)₃ groups and Z is a hydrogen atom or an OH group; and edible salts thereof.

2. A compound according to claim 1 which has the following formula:

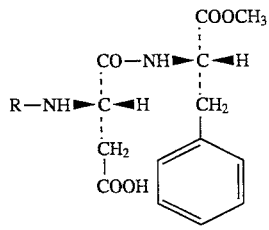

in which R is as defined in claim 1.

3. A compound according to claim 2 which is N-[N-(3,3-dimethylbutyl)-L-α-aspartyl]-L-phenylalanine 1-methyl ester of the formula

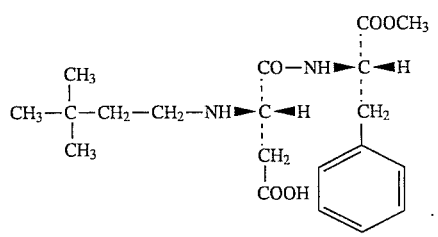

4. A compound according to claim 2 which is N-[N-[3-(4-hydroxy-3-methoxyphenyl)propyl]-L-α-aspartyl]-L-phenylalanine 1-methyl ester of the formula

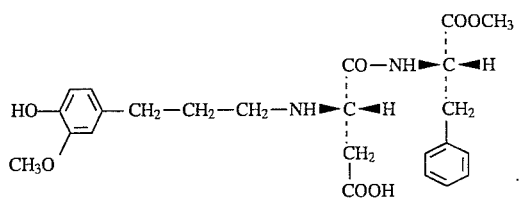

5. A compound according to claim 2 which is N-[N-(3-phenylpropyl)-L-α-aspartyl]-L-phenylalanine 1-methyl ester of the formula

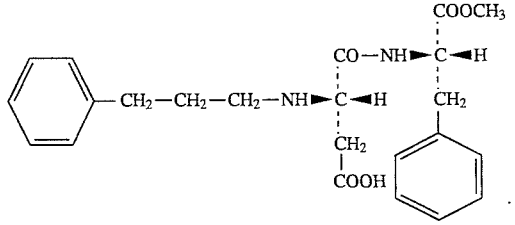

6. A sweetening composition which comprises a compound according to claim 1 as the sweetening agent, in combination with a carrier or a bulking agent.

7. A sweetening composition which comprises a compound according to claim 2 as the sweetening agent, in combination with a carrier or a bulking agent.

* * * * *